(12) United States Patent
Carrieri

(10) Patent No.: US 7,038,789 B1
(45) Date of Patent: May 2, 2006

(54) REMOTE PANORAMIC INFRARED-IMAGING SPECTRORADIOMETER WITH INTEGRATED ENCRYPTED BROADCAST BEACON

(75) Inventor: Arthur H. Carrieri, Abington, MD (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 346 days.

(21) Appl. No.: 10/370,312

(22) Filed: Feb. 13, 2003

(51) Int. Cl.
G01B 9/02 (2006.01)

(52) U.S. Cl. .................................................. 356/491
(58) Field of Classification Search ................ 356/451, 356/453, 491
See application file for complete search history.

(56) References Cited

U.S. PATENT DOCUMENTS

| | | | |
|---|---|---|---|
| 3,977,787 A * | 8/1976 | Fletcher et al. ............. | 356/451 |
| 5,659,391 A * | 8/1997 | Carrieri ....................... | 356/451 |
| 5,708,503 A | 1/1998 | Carrieri | |
| 6,060,710 A | 5/2000 | Carrieri et al. | |
| 6,389,408 B1 | 5/2002 | Carrieri | |

OTHER PUBLICATIONS

Panoramic infrared-imaging spectroradiometer mod . . . , Carrieri, Applied Optics, Mar. 1997, pp 1952-1964.*
Chemical imaging sensor and laser beacon, Carrieri, Applied Optics, Mar. 2003, pp 2772-2784.*

* cited by examiner

Primary Examiner—Gregory J. Toatley, Jr.
Assistant Examiner—Michael A. Lyons
(74) Attorney, Agent, or Firm—Ulysses John Biffoni

(57) ABSTRACT

A passive interferometer chemical sensor and photopolarimeter communicator includes collector and collimator optics, shared solid-state interferometer/photopolarimeter phase-modulation optics, and a lens imager system. The passive interferometer locates, identifies, and tracks an infrared-absorbing vapor in an open panorama by measuring vibration spectrum moiety. The communicator includes a communications beam that is modulated by the shared projected into the same object space from which chemical imaging is preformed. The communications beam provides detection data that is binary encrypted by Mueller matrix-element encoding.

37 Claims, 3 Drawing Sheets

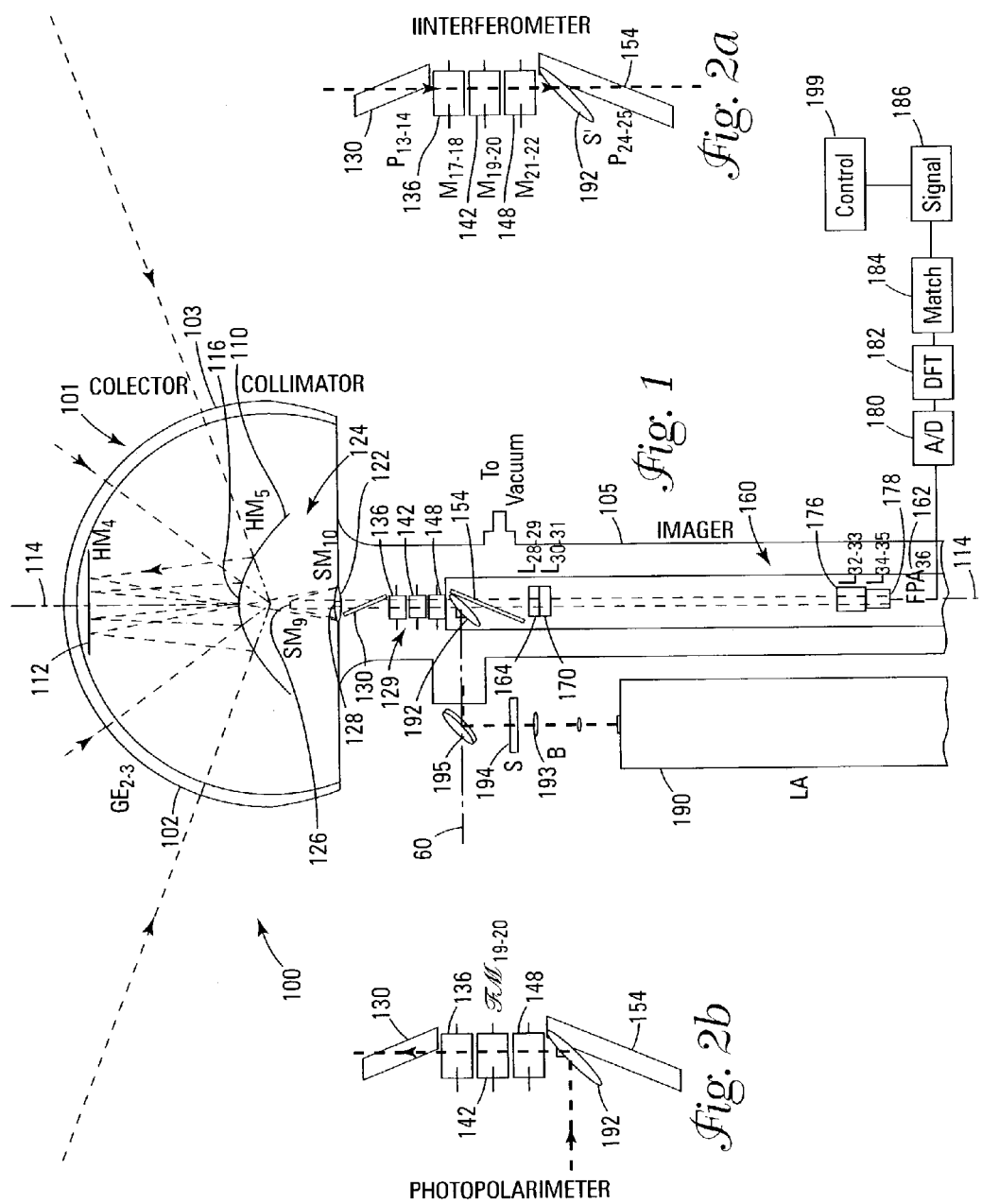

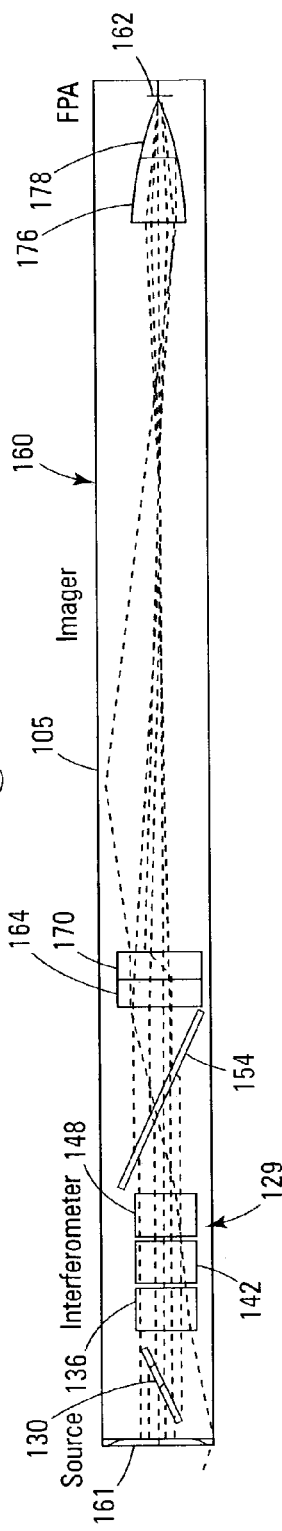
*Fig. 4*
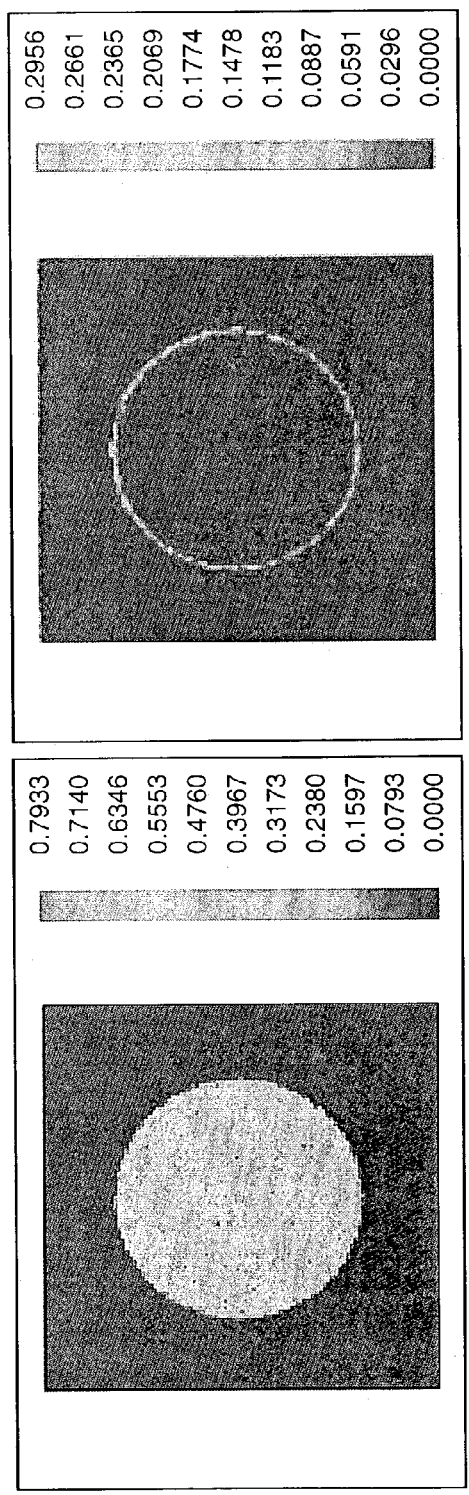
*Fig. 5a*
*Fig. 5b*

REMOTE PANORAMIC INFRARED-IMAGING SPECTRORADIOMETER WITH INTEGRATED ENCRYPTED BROADCAST BEACON

GOVERNMENT INTEREST

The invention described herein may be manufactured, licensed, and used by or for the U.S. Government.

TECHNICAL FIELD

The following description relates in general to the fields of vibrational spectroscopy, spectroradiometry, and Mueller matrix photopolarimetry. In particular, this invention relates to the fusion in a single integrated device of a panoramic chemical imaging sensor that monitors a surrounding infrared panorama for absorption or emission spectra characteristic of various chemical species in order to detect the presence of a chemical cloud, together with a photopolarimeter communicator to broadcast an encrypted signal of its findings modulated and directed by elements that are shared with the chemical imaging sensor.

BACKGROUND

A variety of research projects are involved in design and development of systems for rapid and reliable detection of chemical and biological warfare agents in the field. One such effort, initiated by the U.S. Army in support of the Department of Defense (DoD) Joint Service Wide Area Detection (JSWAD) program, is PANSPEC (short for panoramic-imaging spectroradiometer). Various aspects of PANSPEC systems and designs are discussed in U.S. Pat. No. 5,708,503 issued to Carrieri, on Jan. 13, 1998 ("'503 patent"), U.S. Pat. No. 6,060,710 issued to Carrieri, on May 19, 2000 ("'710 patent") and U.S. Pat. No. 6,389,408 issued to Carrieri, et al., on May 14, 2002 ("'408 patent"). The '503, '710, and '408 patents are incorporated herein by reference as if fully set forth.

Spectral measurements of chemical clouds in the open environment require a sensor of adequate photosensitivity, spectral resolution, numerical aperture and throughput to produce a sufficiently large signal-to-noise ratio for performing useful radiometric detections of such targets. Moreover, for such a device to be of practical value, it must withstand and compensate for extremes in weather, and be sufficiently robust to operate reliably in the field under a variety of adverse conditions.

SUMMARY

In accordance with one aspect, a chemical imaging sensor collects and collimates middle infrared (MIR) radiance over an ambient-environment panoramic field of view (FOV), processes that radiance interferometrically via ultrahigh-speed solid-state birefringent photoelastic modulators (PEM), spatially images the modulated radiance onto a focal-plane array of detector elements, records the measured modulated radiance (i.e., the interferograms) and transforms the interferograms into their corresponding spectra. In accordance with another aspect, the data is processed in parallel using a Fourier transform to yield spectral information. In accordance with another aspect, the chemical imaging sensor analyzes the spectra for the presence of infrared absorption/emission bands characteristic of one or more targeted analytes. In accordance with another aspect, the system performs the analysis via a neural network. In accordance with another aspect, the focal plane array detector provides a matrix of $n^2$ detector elements matched to the size and spatial resolution of the imaged panorama. In accordance with another aspect, spectral information is obtained for each detector element individually, and data from the imaged field as a whole is processed to yield information concerning movement of analytes in the FOV.

In accordance with another aspect, data concerning the analyte is photopolarimetrically relayed into the sensor's panoramic object space via a beacon modulated by a binary Mueller matrix encryption scheme. In accordance with another aspect, the beacon includes an infrared laser that is directed back, at least in part, through system optics shared with the interferometer, to provide an omnidirectional broadcast of the data. In accordance with another aspect, the photopolarimetrically-relayed data includes identity, location, and heading information for analytes. As an active photonics communicator, the sensor utilizes the same PEM optics comprising its passive interferometer component, but the middle PEM is driven in a distinctly different manner such that the instrument becomes a photopolarimeter to an integrated infrared laser continuous-wave beam source. The active photonics communicator, with its advantage of no moving parts and full electro-optical control, modulates the sensor's active carrier beam with encoded binary Mueller matrix elements by driving the middle PEM such that it alternately presents ½ and ¼ waveplates to the active carrier beam. The modulated beam is then directed back through the system optics where it is projected out into the sensor's panoramic object space thus providing an omnidirectional communications capability for the identification and tracking of a chemical vapor threat detected by the interferometer at the focal plane array.

In accordance with another aspect, vignetting of images and stray light analyses are performed to improve image quality. In accordance with another aspect, compensation is provided to account for changes in ambient environment such as temperature, humidity and pressure. In one example, the compensation includes enclosing one or more elements of the system in an evacuated or partially evacuated chamber. In another example, the compensation includes providing a protective index-matched hydrophobic coating. In yet another example, the compensation includes modeling the fluctuations in environmental parameters and providing a compensation model.

BRIEF DESCRIPTION OF DRAWINGS

FIG. 1 is a cross sectional view of optical elements of an infrared-imaging spectroradiometer with integrated encrypted broadcast beacon together with a block diagram of non-optical elements of the system;

FIG. 2(a) shows a cross section of the shared interferometer/photopolarimeter optics configured as an interferometer;

FIG. 2(b) shows a cross section of the shared interferometer/photopolarimeter optics configured as a photopolarimeter;

FIG. 4 shows nonsequential ray-tracing and stray light analyses of core interferometer and imager optics by tracing the paths of five random rays through the optical system from the far left disk collimated ray source to the focal plane array.

FIG. 5a shows a mapping of ~$10^6$ random rays traced through the optical system from source to focal plane array.

FIG. 5b shows maps a mapping of the same ~$10^6$ random rays as in FIG. 5a with an opaque disk object eclipsing the source such that all direct ray paths to the focal plane array are blocked.

DETAILED DESCRIPTION

Figure 3:
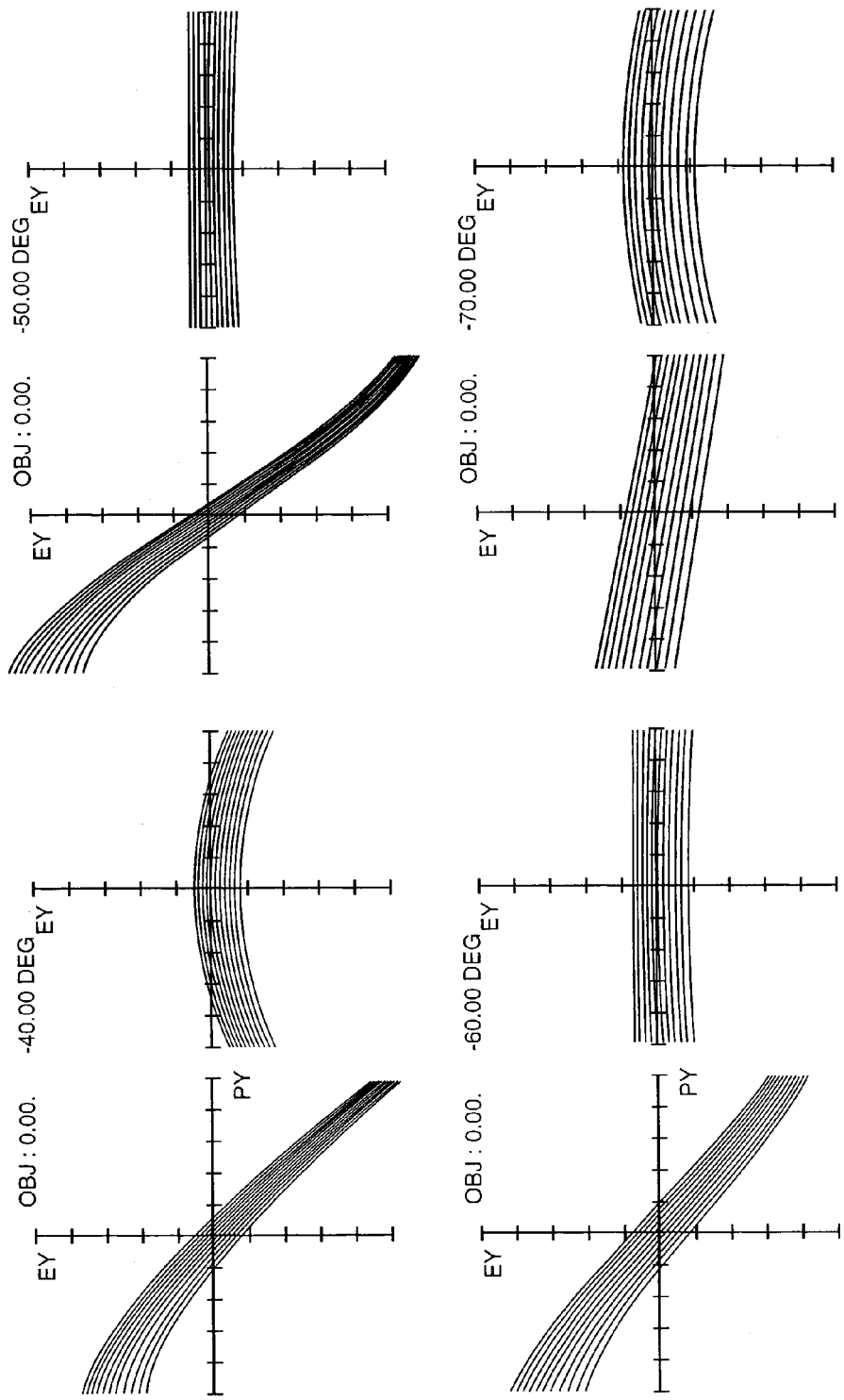
FIG. 3 shows a diagram of image aberrations at the focal plane array of the spectroradiometer system.

In the following detailed description of the preferred embodiments, reference is made to the accompanying drawings that form a part hereof, and in which are shown by way of illustration specific embodiments in which the invention, as claimed, may be practiced. This invention may, however, be embodied in many different forms and should not be construed as limited to the embodiments set forth; rather, these embodiments are provided so that this disclosure will be thorough and complete, and will fully convey the scope of the invention to those skilled in the art. Like numbered elements refer to like elements throughout. As will be appreciated by one of skill in the art, the present invention may be embodied in methods and devices. Accordingly, the present invention may take the form of an entirely hardware embodiment, or an embodiment combining software and hardware aspects.

FIG. 1 shows a section view of the optical elements of a panoramic-imaging spectroradiometer system 100 together with a block diagram of certain non-optical elements of the system. For convenience, surfaces of optical elements are numbered consecutively. The surface numbers are subscripted to symbols of the optical elements to which they relate. For example $Ge_{2-3}$ refers to the outer and inner surfaces, respectively, of the germanium shell 102.

System 100 includes a collector 101 to gather and direct light from a panorama within certain predefined ranges of azimuth and elevation. In the example of FIG. 1, the field of view is bounded by a polar angle of θ=45 degrees and the panorama encompasses the entire surroundings, i.e., 360 degrees. In other embodiments of the invention different polar angles may limit the field of view but the azimuth angle will generally always span the full 360 degrees. Collector 101 includes a primary convex hyperboloid mirror 110 and a secondary concave hyperboloid mirror 112 aligned on a common vertical axis 114. Convex hyperboloid mirror 110 and secondary concave hyperboloid mirror 112 are separated such that the far foci of both mirrors are coincident.

The optical elements of the system 100 are housed within a protective chamber 105 which serves to isolate the sensor from dirt and dust and protect the optics from misalignment that may occur due to changes in pressure, temperature, humidity. The top portion of protective chamber 105 includes a hemispherical Germanium shell 102, which is optimized to minimize aberrations and facilitate the transmission of middle infrared radiance from the panorama. Germanium shell 102 may also include a thin protective index-matched hydrophobic coating 103 to protect system components from changes in ambient humidity.

Light (MIR) passing through Germanium shell 102 is reflected by primary convex hyperboloid mirror 110 to secondary concave hyperboloid mirror 112. Secondary concave hyperboloid mirror 112 reflects the light back in the direction of primary mirror 110 and through an axial opening 116 in primary mirror 110. Axial opening 116 may also include a system stop 118, such as an iris, to adjust the amount of light entering system 100. The light from axial opening 116 next passes through a collimator 124 which aligns the light rays in a direction parallel to vertical axis 114. Collimator 124 is a Schwarzchild collimator and includes a first spherical mirror 122 that reflects the light received from opening 116 to a second spherical mirror 126 that reflects collimated light back through an axial opening 128 of first spherical mirror 122. A correction lens may be included at axial opening 128.

The collimated light emerging from axial opening 128 proceeds downward in a direction parallel to the axis 114 to a series of optical elements that make up the shared interferometer/photopolarimeter optics 129. Interferometer/photopolarimeter 129 is comprised of a first linear polarizer 130 having successive surfaces $P_{13-14}$, a first photo-elastic modulator PEM 136, having successive surfaces $M_{17-18}$, a second PEM 142 having successive surfaces $M_{19-20}$, a third PEM 148 having successive surfaces $M_{21-22}$, and a second polarizer 154 having successive surfaces $P_{21-22}$, which acts as a linear polarizer when the apparatus operates in the passive interferometer mode.

Interferometer/photopolarimeter 129 operates on the principle of stress-birefringence. In the embodiment of FIG. 1, interferometer/photopolarimeter 129 is entirely solid state with no motors, servo mechanisms or rotating or vibrating optical elements, and can operate at substantially greater speed and precision than mechanically-based devices which is essential in order to detect, identify and track rapidly moving and potentially lethal chemical clouds in sufficient time to respond effectively. Moreover, solid-state construction is less susceptible to problems in the field than devices that have moving parts. The PEMs 136, 142, and 148 in the embodiment of FIG. 1 are made of flat, cleaved, ZnSe crystals (ZnSe is the most developed PEM material in the middle infrared range), as shown in FIGS. 2(a) and 2(b), and specified in Table 1 as surfaces 13–25. ZnSe crystals are stress birefringent materials. In a stress birefringent crystal such as ZnSe, the index of refraction in one plane is changed in response to a mechanical stress directed along that plane while the index of refraction in an orthogonal plane remains unchanged. Linear polarized waves with a polarization plane parallel to the plane in which the index of refraction is altered will be retarded when the crystal is compressed, and will be advanced when the material is relaxed. Linear polarized waves with a polarization plane orthogonal to the contraction direction are not influenced. Piezoelectric transducers bonded to opposite, parallel, planar surfaces of the ZnSe crystal ends introduce the mechanical stresses in PEMs 136, 142, and 148. Application of a time varying periodic electric field to the piezoelectric transducers causes the crystals to compress-then-relax, thereby oscillating the refractive index quantity in the crystal plane along its extraordinary axis, further causing an oscillating phase contrast in the electric field traversing that direction along the extraordinary axis relative to an orthogonal field component traveling concurrently along the ordinary axis of the crystal.

All optics of interferometer/photopolarimeter 129 are antireflection-coated to yield MIR transmissions exceeding 0.95. In this example, PEMs 136, 142 and 148 are commercially available ZnSe modulators that produce spectra approximately 20 cm$^{-1}$, (wavenumbers) in resolution, a generally adequate resolution to detect the fundamentally broad MIR vibration bands of relatively large nerve agent molecules. The birefringence quantity in the modulating crystals of the interferometer is directly proportional to resolution of its spectral content from the interferogram output. Hence, to measure detail in the more narrow structural bands of chemical warfare agent compounds of lesser molecular weight (i.e., the blood agents HCN, CNCl, . . .

etc) either the interferometer must accommodate additional ZnSe PEMs for added birefringence, or crystalline materials with a stronger birefringence property (i.e., increased phase retardation when stressed) need to replace the ZnSe windows.

The crystal elements of PEMs 136, 142 and 148 are compressed-then-relaxed at their natural mechanical resonance frequency ω by the piezoelectric transducer elements T. This action causes an oscillating phase difference (due to relative optical path differences) in two mutually coherent sets of infrared electromagnetic field waves that are perpendicular to each other. One electric field component is made to vibrate along the crystal's "fast" axis (ordinary component, $E^o_{in}$) whereupon its phase character is constant on transmission through the crystal. The other, perpendicular, component lies along the crystal's "slow" axis (extraordinary component, $E^{eo}_{in}$) and possesses an oscillating retardation or phase delay, δ in response to the mechanical compressions induced by the piezoelectric transducer elements T. Accordingly, $\delta = \delta_0 \cos \omega t$, where $\delta_0$ is the maximum amplitude of phase retardation induced by the ZnSe crystal via transducer element T and ω is the natural mechanical resonance frequency of the crystal. These orthogonal components combine at the back surface of each crystal, sweeping a continuum of polarization states in the electric field vector at its exit boundary (modulating Stokes vector), and thereby producing a temporal (t) intensity output signal by the interferometer optical system in the functional form of $I_f(v,t:\omega_m,\omega_n,\omega_1) \propto |E^{eo}_{in} + E^o_{in}|^2$ called an interferogram. This interferogram data record is modulated at the MIR energy (v) with fundamental and overtone frequencies ($\omega_m,\omega_n,\omega_1$) of the respective driven optics of PEMs 136, 142 and 148. This form of modulation is a manifestation of the piezoelectric tensor T operating on opposite ends of the PEM crystals called stress birefringence: a generator of the interferogram voltage waveform $I_f$. PEM interferometry is analogous to Michelson interferometry, however, in PEM interferometry, phase retardation is accomplished electro-optically via stress-birefringent crystals whereas Michelson interferometry requires an oscillating mirror or inertial spinning prism phase-shifter.

After the incident light has passed through the various elements of the shared interferometer/photopolarimeter optics 129 it is focused by imager 160 onto a focal plane array 162 of photo detectors having a surface $FPA_{36}$. Imager 160 includes four lenses arranged in a doublet with a first lens 164 having successive surfaces $L_{28-29}$, a second lens 170 having successive surfaces $L_{30-31}$, a third lens 176 having successive surfaces $L_{32-33}$, and a fourth lens 182 having successive surfaces $L_{34-35}$. The focal plane array 162 is made from mercury- cadmium-tellurium (HgCdTe) pixel detector elements. The doublet lenses of imager 160 are made from zinc selenium germanium ZnSeGe optimized for minimum aberration and maximum resolution of a distant chemical cloud object imaged from panoramic object space.

FIGS. 2(a) and 2(b) show interferometer/photopolarimeter optics 129 in greater detail. In this example, PEMs 136, 142 and 148 include stress-birefringence ZnSe crystals driven at mechanical resonance frequency by piezoelectric elements and are positioned between linear polarizers 130 and 158 (vis-à-vis ZnSe or Ge plates angled at their Brewster angle). This optical array performs passive thermal interferometry via a triple polarization-modulation operation by the PEMs on throughput infrared radiance collected and collimated over the instrument field of view. Infrared spectra are measured simultaneously at each HgCdTe pixel element of an n×n square detector focal plane array 162 cooled by liquid nitrogen (the cooling temperature of liquid nitrogen enhances infrared photosensitivity of the pixel HgCdTe semiconductor material) and matched to the open environment imaged panorama. Each pixel element of the focal plane array 162 produces a time varying electrical signal. The signals output by focal plane array 162 are digitized by parallel analog to digital converter circuits 180, processed in parallel by a spectrum analyzer indicated at 182, and each of the processed spectra are respectively matched against spectral patterns for chemical contaminants of interest in a pattern recognition operation indicated at 184. In one embodiment the spectrum analyzer performs a discrete Fourier transform to yield spectra for each signal from the focal plane array. Thus, each electrical signal provided by the focal plane array 162 (i.e., the pixels in the image) yields "Stokes Parameters" which represent complete polarization information for a location in the panorama. The polarimetry information provided by system 100 is much more efficient than a point-by-point scan, as was required in some previous polarimetry techniques based on PEMs. Because elements of focal plane array1 62 subtend contiguous solid angles in the FOV, those localized pixels that yield fingerprint absorption or emission bands of a chemical vapor mass will also provide information on its volumetric location and movement such as the cloud's heading and speed of travel or dispersion. The system 100 provides $n^2$ interferograms, one per pixel element of the focal plane array 162, that are acquired with a parallel architecture of analog-to-digital signal converter circuits 180.

These interferogram data records are simultaneously analyzed at 182 into infrared spectra and compared with known data by a pattern recognition operation 184 multiplexed to this architecture. The pattern recognition operation 184 performs pattern recognition of absorption or emission band moieties from one or a group of pixels as the chemical cloud intercepts, proceeds through, and exits the sensor FOV. In one embodiment the pattern recognition operation 184 comprises a neural network such as the neural network system described in the '408 patent, incorporated herein by reference.

Following an absorption/emission vibrational spectrum match by the pattern recognition operation 184 a signal such as an alarm 186 is provided to alert users of the presence of a chemical or biological hazard. Post-processing functions such as a spatial mapping of the chemical gas and instructions on dealing with toxic properties associated with the detected chemical may also be provided.

The imager 160 and focal plane array 162 illustrated in FIG. 1 are also specified as lens surfaces 28-35 in Table 1, with the focal plane array surface $FPA_{36}$ lying just beyond lens surface 35. These parameters have been optimized based on the following: (1) input fields θ={(0, ±37°), (0, ±42°), . . . (0, ±67°), (0, ±70°)}; (2) two-layered antireflection coatings (HEAR2) on lens surfaces; (3) the vignetting factors of Table 2 (vignetting is a distortion of the paraxial entrance pupil or EP, and a significant aberration for wide-angle imaging systems); (4) the refractive indices of ZnSe and Ge over the 8–12 μm MIR band; (5) a merit function (MF) that limits coma, field curvature, and distortion of image ($3^{rd}$ order Seidel coefficients); (6) a MF accepting image resolution of 45 line-pairs per millimeter resolution and Modulation Transfer Function (MTF) values between 0.3–0.5 for all field angles θ; and (7) a MF that prevents rouge or impossible designs (such as run away thickness and negative thickness on optics, etc).

FIG. 3 shows the results of a transverse ray fan plot of image aberrations at the focal plane array 162 at field angles ranging from −40.00 degrees to −70.00 degrees. Optimization has consistently migrated toward the imager 160 depicted in FIG. 1, where the front doublet of lenses 164 and 170 (lens surfaces 28–31, Table 1) is separated by a relatively large air gap from the back doublet of lenses 176 and 178 (lens surfaces 32–35, Table 1). Field curvature, coma and distortion are its most significant image-degrading aberrations. Field curvature, the inward change of focus with field angle, is defined by a $W_{220}h^2r^2$ term of the wavefront expansion function (viz, change of slope in the linear portion of EY(PY) with field angle, FIG. 3). Coma is a change in image magnification with aperture, defined by the expansion coefficient $W_{131}hr^3 \cos \theta$ (viz, change of curvature in the parabola portion of EY(PY), FIG. 3). Barrel distortion is an inward shift in the location of image with field angle, $W_{311}h^3r\cos \theta$. As FIG. 3 demonstrates, the doublet design of imager 160 minimizes severe $3^{rd}$ order aberrations yet also maintains an appreciable optical throughput (since the number of lens components of imager 160 are held to a minimum). A sufficiently high throughput is needed for detecting spectral signatures of chemical clouds estimated to be in the parts-per-thousand or less concentration of imaged MIR radiance.

Tolerance analysis (TA) evaluates fabrication and alignment errors expected to occur when shaping system optics, and the mounting of these optics as single and grouped elements. A major performance metric of the TA is peak Modulation Transfer Function (MTF) over the MIR wavelengths of 8–12 μm. In performing a TA, variances are placed on optimized parameters defining the geometry of system optics, and on irregularities in their decentration and indices of refraction. The fabrication parameters under test include: radius of curvature, thickness, and conic constant; while the alignment parameters include: lateral translation, air space, tilt, spin and roll. Thickness of back focus (i.e., location of the focal plane array, surface 36, Table 1) was the compensator surface used in this TA. This compensator surface parameter is a sort of 'relief valve' diagnostic of the TA, easing overly constraining tolerances on the critical optics most sensitive to change in the MTF metric. Thus, a small air gap between surface 35 of lens 178 and focal plane array 162 can be provided in the final assembly stage of manufacturing the sensor of FIG. 1. Variances on all of the general parameters mentioned above were loosely set in an initial run of the TA, so as to insure that the optical system could be manufactured within these relatively loose specifications. The initial TA run produced a list of worst offender optics, i.e., the optics with perturbations that contribute most to image degradation and negative system performance. In succeeding TA trial runs, variances on these worst offender optics were systematically tightened (usually halved) ad fin, until the MTF metric set in the TA (set to yield an acceptable image quality) was approached and met, and in some cases, exceeded.

The TA initially proceeded along these lines of assigned variances on all single and paired optics: ±0.1% radius of curvature, ±0.001 inch on thickness and airspace, ±10.1% conic constant, ¼ wave surface error, ±0.001 inch vertical-horizontal decentration, ±0.001 inch back focal distance, and ±50 arc-second vertical-horizontal tilt. Under the above tolerances, a sensitivity test was performed for: a test wavelength of 10.6 μm; a MTF nominal spatial frequency test value of 40 line-pairs per millimeter; a sampling of conjugate image rays over a 128×128 grid of averaged tangential and sagittal rays launched from and over the EP; and a sum total of 20 Monte Carlo simulations. (A Monte Carlo simulation was used to estimate image performance by simultaneously perturbing all optics tagged for this TA.) The sensitivity resulted in an image performance of mean MTF=0.37±0.012 (standard deviation) for the following five worst offender optics: [30, TFRN, 0.025]; [32, TFRN, 1.000]; [2, TSTY, −0.025]; [2, TSTY, +0.025]; [30, TSTX, 0.100]; where the entries in brackets are the optic surface number of Table 1, the tolerance operand (TFRN=curvature in fringes, TSTY[X]=horizontal[vertical] tilt in degree), and the tolerance quantity, respectively. Tightest tolerances (of most concern to an optics fabricator) appeared to reside in curvature and tilt of the imager doublets (±1 fringe, ±0.100°), tilt of the collector Ge dome (±0.025 deg), and tilt of the collector-collimator conic mirrors (±0.025°), in that order. Clear panoramic imagery may be expected, provided that fabrication and mounting specifications are maintained or exceeded. Fabricating the system to less critical specifications on the remainder optics would then follow.

Operating the system 100 continuously in the open atmosphere introduces several challenges regarding the maintenance of good image performance. They include diurnal swings of refractive index in ZnSe and Ge optics and the expansion/contraction of optical materials (and their mounts) as environmental pressure and temperature states fluctuate. These phenomena can be modeled in a manner similar to the tolerance-sensitivity analysis mentioned above. However, if the inner volume from dome 102 to focal plane array 162 is placed in enclosure 105 that provides a stable atmosphere, partial vacuum or vacuum, then undesired image-degrading effects brought on by changing atmospheric conditions may be improved. Finally, a thin protective index-matched hydrophobic coating 103 on the outside surface of dome 102 will improve operation in an ambient environment of high relative humidity.

Various system deficiencies are not well modeled by the computer sequential ray-tracing (SRT) procedure used to design the system parameters of Table 1. For example, the SRT method ignores rays that undergo total internal reflection (TIR); where a ray totally reflects at a surface boundary separating more-dense and less-dense media, provided that ray is incident to the surface from the more-dense side and beyond a critical angle. Generally, the SRT method is invalid for tracking multiple ray-paths, as when a ray splits and undergoes multiple reflections at an interface whereby that surface, and possibly several other surfaces of the optical system, become illuminated in a nonsequential order. Moreover, SRT cannot be applied to the problem of diffuse scattering and blackbody (or colored body) emittance, as rays tend to liberate from an optically rough irradiation zone in a uniform Lambertian-like angular distribution. The image performance of an optical system is potentially compromised by such phenomena. Therefore, nonsequential ray paths traversing the system must be tracked for the benefit of analyzing stray light (i.e., the indirect and undesired scattering/emission of light) and ghost imaging (via TIR, scattering, and/or multiple reflections from PEM windows, polarizer plates, and lens surface components) at its focal plane array 162. Baffle structures to intercept stray light may be positioned in optical systems based on nonsequential ray-tracing (NSRT) analysis and identification of stray light source paths. Nonsequential ray-tracing analysis can also identify optical surfaces requiring a high transmission (anti-reflection) coating layer(s) that would effectively attenuate or eliminate ghost images at or in the neighborhood of the image plane.

A nonsequential ray-tracing model was used to globally track rays undergoing TIR, multiply reflections, and/or diffuse scattering in this model design. FIG. 4 illustrates an example of the nonsequential ray-tracing model system. The sequential optical surfaces 10–36 of Table 1 were converted into a nonsequential ray-tracing optical components group. Next, cylindrical enclosure 105 was added to the model enclosing these interferometer-imager-focal plane array nonsequential ray-tracing receiver optical elements as described above. Enclosure 105 was modeled to include a reflective Lambertian inner surface (a value of 0.55 was used for the scatter function with a selection of 5 scattered rays), 18.5 mm inner radius, and 520 mm length starting at surface 10 and extending just beyond the focal plane array 162, surface 36, Table 1. A disk illumination source 161 was included in the model at the opposite end of enclosure 105 from focal plane array 162, aligned on axis and directing collimated light down the full volume of the enclosure encompassing the nonsequential ray-tracing receiver optics group. Disk illumination source 161 simulates the collimation function of Schwarzchild optics, surface 9–10, Table 1). Finally, a nonsequential ray-tracing absorbing detector of 2.25 mm$^2$ surface area and composed of 100×100 pixel elements was positioned at the exact focal plane array location to model the focal plane array 162.

In the simulation, 10$^6$ random rays were traced through the model system. FIG. 4 shows tracking of 5 such random rays launched from the disk illumination source through the linear interferometer-imager-focal plane array optical system. In this illustration, TIR occurs between the polarizing element surfaces 24-25 as well as at the final lens surface 35 of lens 178, where the latter TIR ray gets scattered at the wall of enclosure 105 and eventually exits the enclosure 105 to the left. Two results of tracing 10$^6$ random rays from disk source to nonsequential ray-tracing detector are shown in FIGS. 5(a) and 5(b). The disk source is unobstructed in FIG. 5(a), while FIG. 5(b) shows the effect of eclipsing the illumination source with an obstacle of diameter equal to that of the Schwarzchild collimator's secondary spherical mirror, surface 10 of Table 1. This obscuration blocks all direct ray-paths from illumination source 161 to focal plane array 162. A comparison between FIG. 5(a) and FIG. 5(b) indicates that the system 100 is practically free of stray light. Thus, although a stray-light baffle structure could be included it should not be needed.

Ghost images appear primarily as multiple-path light reflections by one or several of the doublet lens surfaces 28–35, Table 1. With two-layered antireflection coatings placed on all imager lens surfaces, a ghost image analysis was conducted on the receiver nonsequential ray-tracing interferometer-imager-focal plane array optical group. A nearest ghost image of a real surface object (with pupil), with appreciable intensity, was found to be present at a location of –47.35 mm (left, on-axis) from the focal plane array 162. This is sufficiently removed from the focal plane array 162, and provides positive assurance that the system specified in Table 1 is removed of ghost imaging interference.

The photonics communication feature or active broadcast beacon of the system 100 enables rapid communication of sensor data to a variety of receivers. Information is optically transmitted to all points in the panorama that are within reasonable range in the following manner. A thin beam of collimated light exiting laser 190 is first expanded at telescopic lens system 193-194 to increase the diameter of the laser beam to that of the collimated radiant beam (directed by the Schwarzchid collimation optics to the FPA, in the spectroradiometer mode). That collimated beam is directed along the axis 60 to polarizer 154. The polarizer 154 linearly polarizes the collimated beam received along the axis 60 and directs it upward along the axis 114 to the PEM 148. As the collimated light passes through PEM 142 its amplitude and phase is changed by modulation provided by the controller 199 to PEM 142 so that the instrument as shown in FIG. 2(b) now acts as a photopolarimeter.

As a photopolarimeter, the end PEMs 148 and 136 ($M_{21\text{-}22}$ and $M_{17\text{-}18}$) modulate in exactly the same way as when the system operates in its passive interferometer mode, while the middle PEM optic $\mathfrak{M}=\mathcal{M}_{9\text{-}20}(\lambda/2|\lambda/4)$ is now driven into alternate half-waveplate $\mathcal{M}_{19\text{-}20}(\lambda/2)$ and quarter-waveplate $\mathcal{M}_{9\text{-}20}(\lambda/4)$ states. The particular photopolarimeter configuration of FIG. 2b, with optical elements of order [$P_{24\text{-}25}$, $M_{21\text{-}22}|M_{17\text{-}18}$, $P_{13\text{-}14}$], as they are fixed in that relative orientation, produces a polarogram that carries 8 of 16 Mueller matrix elements of $\mathfrak{M}$ in the laser beam exiting the dome 102. (This waveform is similar to the interferogram data records of the ambient MIR radiant field produced at the focal plane array 162, when the device operates as a passive spectroradiometer). Specifically, four exact orientations of the end paired-optics of FIG. 2(b) produce the matrix elements $\mathfrak{M}$ as depicted in Tables 3–6, and described as follows.

A number of different orientations of the axes of the optical elements of combined interferometer/photopolarimeter 129 are possible. The particular orientation will determine which elements of the Muller matrix are used for photopolarimeter communication. Four cases (A, B, C, and D) are examined in Tables 3, 4, 5 and 6. For example, in Table 3 (case A), orientations of the photopolarimeter optics of polarizer 130, PEM 136, PEM 148 and polarizer 154 are vertical, –45°, +45°, and vertical, respectively, relative to optical axis 114. In this configuration communication takes place over the $M^{34}$ matrix element. In Table 4 orientations of those same elements are vertical, –45°, vertical, and –45°, enabling binary communications over the $\mathfrak{M}^{34}$ and $\mathfrak{M}^{44}$ elements. Tables 5 and 6 likewise examine two other possible orientations.

In one embodiment, the laser 190 of system 100 is of the waveguide cavity design variety, producing a continuous-wave $CO_2$ source beam operating on the (hot) P20 line at 10.6 µm wavelength, 10-50 watts beam power. This waveguide laser source was chosen because the technology is mature (high beam spatial mode stability and relatively short coherence length) and beam power is sufficiently large (the beam is made to spread over a rather large- volume FOV) so that long-range detection is made possible over a wide solid angle in panoramic object space. (Along with beam intensity, range at which the beacon light is detected depends on atmospheric transmission, infrared sensitivity of the detector element used in the remote receiver, gain of that detector's amplifiers and other electronics factors.) Other laser sources may also be employed. For example, an infrared laser based on solid-state diode technology, can replace the waveguide $CO_2$ system with less bulk, cooling requirements, and power consumption. However, range of the beacon will be reduced because of reduced beam intensity available for transmission. Furthermore, quality of beam encryption may be compromised on account of the generally poor temporal and spatial coherence of laser diode light with possible spatial mode-hopping behavior.

The polarogram beacon passed back into the panorama is derived from the following photopolarimeter system matrix equation:

$$\psi = P_{13\text{-}14} M_{17\text{-}18} \mathfrak{M} M_{21\text{-}22} P_{24\text{-}25} \quad \text{(Eq. 1)}$$

where subscripts represent optical surfaces as listed in Table 1, P and M are the Mueller matrices of polarizers 130 and 154, respectively, and Mueller matrix $\mathfrak{M}$ has elements of the PEM 142 (which acts as a switching waveplate) $\mathcal{M}_{19\text{-}20}(\lambda/2, \lambda/4)$ given by:

$$\mathcal{M}_{19\text{-}20}(\lambda/2) = \begin{pmatrix} 1 & 0 & 0 & 0 \\ 0 & \cos^2 2\alpha - \sin^2 2\alpha & 2\cos 2\alpha \sin 2\alpha & 0 \\ 0 & 2\cos 2\alpha \sin 2\alpha & \sin^2 2\alpha - \cos^2 2\alpha & 0 \\ 0 & 0 & 0 & -1 \end{pmatrix} \quad \text{(Eq. 2)}$$

$$\mathcal{M}_{19\text{-}20}(\lambda/4) = \begin{pmatrix} 1 & 0 & 0 & 0 \\ 0 & \cos^2 2\alpha & \cos 2\alpha \sin 2\alpha & -\sin 2\alpha \\ 0 & \cos 2\alpha \sin 2\alpha & \sin^2 2\alpha & \cos 2\alpha \\ 0 & \sin 2\alpha & -\cos 2\alpha & 0 \end{pmatrix}, \quad \text{(Eq. 3)}$$

where $\alpha$ is the azimuth angle orientation in the middle ZnSe crystal relative to its fast axis (see the above text).

The Mueller matrices $\mathfrak{M} = \mathcal{M}_{19\text{-}20}(\lambda/2, \lambda/4)$ are measured in a sequence of compressions by the piezoelectric tensor $\mathcal{T}_{19\text{-}20}$ of PEM 142 that enacts precise stress amplitudes in the ZnSe material causing, respectively, ½- and ¼-wave retardations in a laser beam whose electric field oscillates in a plane along the crystal's extraordinary axis. Pulse duration of the incident laser beam is set by a chopping action of shutter 192 as it is gated to those exact periods of ½- and ¼-wave retardations in $\mathfrak{M}$. The gated beam pulse duration must be sufficiently long compared to the modulation periods of PEMs 148 and 136 ($M_{21\text{-}22}$ and $M_{17\text{-}18}$) so that electronic lock-in measurement of the Mueller matrix elements $\mathfrak{M}$ can be resolved (by a digital or analog electronic acquisition system) from the polarogram waveform in real-time.

The system matrix $\psi$ given by Equation 1 transforms the incident beam Stokes vector ($s^i$) preset by polarizer 154 ($P_{24\text{-}25}$) into the transmitted beam Stokes vector ($s^t$) preset by polarizer 130 $P_{13\text{-}14}$ accordingly:

$$s^t = \psi s^i. \quad \text{(Eq. 4)}$$

The normalized intensity of the polarogram takes the following form when substituting Eq. 1 into Eq. 4, inserting known values of the matrix elements of M, P and s, utilizing a Bessel generator function to express modulating element terms in the Mueller matrices $M_{17\text{-}18}$ and $M_{21\text{-}22}$, and expanding, then factorizing, this resultant function.

$$I/I_0 = \psi_{1,1} + I(\omega_1, \omega_2) \quad \text{(Eq. 5)}$$

$$I(\omega_1, \omega_2) = \psi_{i,j} \left[ \sum_{n=0, m=0}^{2} C_{n,m} \cos(\pm n\omega_2 t \pm m\omega_1 t) + \sum_{n=3, m=3}^{\infty} \Theta^h \{\cos(n\omega_1 t, m\omega_2 t)\} \right] \quad \text{(Eq. 6)}$$

The normalized elements of $\mathfrak{M}$ can be expressed as $\psi_{i,j}/\psi_{1,1}$, as the $\psi_{1,1}$ element has no polarization dependence and is referred to as the dc component of the polarogram. $I(\omega_1, \omega_2)$ is the polarogram's Fourier expansion representing primary circular frequencies ($\omega^1, \omega_2$) of $M_{17\text{-}18}$ and $M_{21\text{-}22}$, respectively, and their overtones ($n\omega_1, m\omega_2$). It is referred to as the ac component of the polarogram. The amplitude coefficient of each frequency component of order two or less in $I(\omega_1, \omega_2)$ is $C_{n,m}$, as these dominant harmonics are grouped in the first summation term to the right in Equation 6. These terms comprise a zero, product of two (zero and first order coefficients), and product of three (zero, first and second order coefficients) Bessel function factors whose arguments have a fixed retardation $\omega_0 = 2.404$ rad, and a factor that is one of eight Mueller matrix elements $\psi_{i,j}$ of the waveplates $\mathfrak{M} = \mathcal{M}_{19\text{-}20}(\lambda/2|\lambda/4)$. All higher harmonics beyond second order are grouped in the second summation term to the right in Equation 6. This equation, therefore, represents an infinite series expansion in terms of all primary and overtone modulation frequencies, namely, the sums and differences of all integral multiples of the frequencies of PEMs 136 and 148, which can range between 10–100 KHz for ZnSe, and are typically offset ~2 KHz. Those frequencies in $I(\omega_1, \omega_2)$ that are $2^{nd}$ order (in $C_{n,m}$) and below are locked into as the dominant intensities of the Fourier components. In other words, the second summation of Equation 6 is dropped, since these harmonics monotonically reduce intensity of the Mueller matrix coefficients, tagged by their respective PEM overtones, below signal-to-noise levels of those HgCdTe pixel elements comprising the focal plane array 162. Determination of the Mueller elements of Equations 2 and 3 is thus equivalent to the measurement of those amplitudes of the corresponding frequency components of Equation 6 that lock into their respective matrix elements as shown in Tables 3-6. In one example, this measurement is accomplished with an electronic circuit of analog multipliers and filters. Digital signal processing may also be used in other examples. The circuit will accept sum and difference reference modulation frequencies, one at the driving frequency and the other at twice the driving frequency of $M_{21\text{-}33}$ and $M_{17\text{-}18}$. For example, to generate reference frequency ($2\omega_2 + \omega_1$) necessary for lock-in measurement of the [3,4] element of $\mathfrak{M}$, Table 4, both $2\omega_2$ and $\omega_1$ signals from the PEM controller 199 (cos $2\omega_2 t$ and cos $\omega_1 t$) are input to a multiplier circuit, which generates an output of ½{cos($2\omega_2 - \omega_1$)t + cos($2\omega_2 + \omega_1$)t}. A high-Q filter located at the output end of this multiplier circuit will subsequently transmit the desired overtone while suppressing the other.

A complete set of primary and overtone frequencies shown in Tables 3-6 is generated in this manner, from combinations of $\omega_1$, $\omega_2$, $2\omega_2$, and $2\omega_2$ outputs by the multiplier circuit. These reference frequency waveforms are input to their respective lock-in amplification (LIA) circuit channels, one per reference frequency with a total of eight LIA circuits. The other LIA circuit input is the amplified polarogram signal (Equation 6), as detected from the active laser carrier beam, via a remote receiver. The LIA multiplies this polarogram data record together with all individual reference frequencies (see above), producing a voltage output signal that is proportional to the amplitude of the polarogram, at that particular reference frequency, times a phase factor. This signal is proportional to the binary Mueller matrix elements $\mathfrak{M}$ as shown in Tables 3–6 (with proportionality constant $C_{n,m}$). It is these binary elemental signals from which decoding of the source beam encryption is established. In particular, it is the binary states of the fourth-quadrant elements $\mathfrak{M}^{33}[-1,0]$, $\mathfrak{M}^{34}[0,-1]$, $\mathfrak{M}^{43}[0,1]$, and $\mathfrak{M}^{44}[-1,0]$ that are of interest here for beam encoding purposes.

An optical receiver staring at, and within the FOV of the photopolarimeter system, is thereby capable of measuring this encryption if properly equipped with the appropriate telescope, infrared detector, amplifier, and phase-sensitive electronics as described above. For example, if the system optics [$P_{24\text{-}25}$, $M_{21\text{-}22}$|$M_{17\text{-}18}$, $P_{13\text{-}14}$] are orientated as [+45°, vertical | vertical, −45°] (Table 5) and a remote aircraft, lying within its FOV and staring at the beacon, locks into element $\mathfrak{M}^{33}[-1,0]$ and its compliment element $\mathfrak{M}^{34}[0,-1]$.

After a focal plane array 162 pixel group reveals spectral identification of a noxious vapor target over timeframe τ, the system changes into its photonics communications mode and transmits a binary code in its laser carrier beam through the one or more Mueller matrix channels. For example in Table 5 (Case C) configuration, a communications would take place over the $2\omega_2 - 2\omega_1$ channel (the $\mathfrak{M}^{33}$ measurement). A properly encrypted binary sequence gathered by a suitable receiver will decode data concerning the analyte and its movement. This data may include the heading of the vapor cloud by encoding those coordinates in pixels of the focal plane array 162 that produced the analyte spectrum—via the interferometer in the passive spectroscopy measurement timeframe τ. Physical properties of the cloud analyte such as molecular weight, nomenclature, toxicity, . . . etc, can follow in some encoded sequence of $\mathfrak{M}^{33}$bits. In addition, in the example in Table 5, a simultaneous conformation of these data bits would reside over the complimentary channel $\omega_1+2\omega_2$ (the $\mathfrak{M}^{34}$ measurement) and serve, for instance, as a check for parity errors in the encryption.

CONCLUSION

The system of the present invention provides a simple lens configuration with good image performance for spectroscopic operation and in which practical tolerances of optics, vignetting, ghost imaging, and stray light were analyzed for the benefit of preserving that good image quality for continuous operations of long duration. To maintain good image performance as the sensor operates continually in an environment of changing pressure and temperature the sensor may be enclosed within a cylindrical sleeve, encompassing internal optics and structural supports, and placing the cylindrical volume under a vacuum, partial vacuum or stable pressure and equipped with temperature stabilizing elements to provide heating and cooling as necessary. As an active photonics communicator, the beacon facilitates an omnidirectional alert of conditions presented by a chemical vapor threat. The location and heading of that threat may be communicated into the environment over a wide-angle field-of- view via a carrier beam such as a laser, modulated with binary encrypted Mueller matrix-element encoding by a photopolarimeter comprising one or more photoelastic modulator elements.

A number of embodiments of the invention defined by the following claims have been described. Nevertheless, it will be understood that various modifications to the described embodiments may be made without departing from the spirit and scope of the claimed invention. Accordingly, other embodiments are within the scope of the following claims.

TABLE 1

Example design parameters.

| SURFACE | CURVE ($mm^{-1}$) | THICK (mm) | GLASS | SEMI-DIAMETER (mm) | CONIC | X-AXIS TILT (deg) | Coating |
|---|---|---|---|---|---|---|---|
| 0 Object Space | 0. | Infinity | | | | 0. | |
| 1 | 0. | −181.41369 | | 0.37149 | | 0. | |
| 2 Dome Front | 0.00551 | 9.52500 | Ge | 181.38617 | 0. | 0. | AR2[i] |
| 3 Dome Back | 0.00581 | 141.98300 | | 171.86262 | 0. | 0. | AR2[i] |
| 4 Collector Primary | 0.01531 | −132.69600 | Mirror | 81.04903 | −1.40184 | 0. | ALUM[j] |
| 5 Collector Secondary | 0.00151 | 132.69600 | Mirror | 45.58323 | −15.70057 | 0. | ALUM[j] |
| 6 Aperture Stop[a] | 0. | 0. | | 2.14194 | | 0. | |
| 7 | | 45.22374 | | | | | |
| 8 Obscuration[b] | 0. | 44.26241 | | 9.69505 | | 0. | |
| 9 Collimator Primary | −0.01428 | −43.26241 | Mirror | 18.39512 | 0. | 0. | ALUM[j] |
| 10 Collimator Secondary | −0.03512 | 43.26241 | Mirror | 4.34250 | 0. | 0. | ALUM[j] |
| 11 | | 20.00000 | | | | | |
| 12 Coordinate Break | | | | | | 67.4[h] | |
| 13 Polarizer Plate 1 Front[c] | 0. | 3.04800 | ZnSe | 15.00000 | 0. | 0. | AR2[i] |
| 14 Polarizer Plate 1 Back[c] | 0. | 0. | | 15.00000 | 0. | 0. | AR2[i] |
| 15 Coordinate Break | | | | | | −67.4[h] | |
| 16 | | 20.00000 | | | | | |
| 17 PEM 1 Front[d] | 0. | 15.87500 | ZnSe | 10.00000 | 0. | 0. | AR2[i] |
| 18 PEM 1 Back[e] | 0. | 2.00000 | | 10.00000 | 0. | 0. | AR2[i] |
| 19 PEM 2 Front[d] | 0. | 15.87500 | ZnSe | 10.00000 | 0. | 0. | AR2[i] |
| 20 PEM 2 Back[e] | 0. | 2.00000 | | 10.00000 | 0. | 0. | AR2[i] |
| 21 PEM 3 Front[d] | 0. | 15.87500 | ZnSe | 10.00000 | 0. | 0. | AR2[i] |
| 22 PEM 3 Back[e] | 0. | 35.00000 | | 10.00000 | 0. | 0. | AR2[i] |
| 23 Coordinate Break | | | | | | 67.4[h] | |
| 24 Polarizer Plate 2 Front[f] | 0. | 3.04800 | ZnSe | 34.70301 | 0. | 0. | AR2[i] |
| 25 Polarizer Plate 2 Back[f] | 0. | 0. | | 36.00890 | 0. | 0. | AR2[i] |
| 26 Coordinate Break | | | | | | −67.4[h] | |
| 27 | | 34.99967 | | | | | |
| 28 Doublet A Lens 1 Front | −0.00239 | 9.999936 | ZnSe | 13.93226 | 0. | 0. | AR2[i] |
| 29 Doublet A Lens 1 Back | −0.00328 | 0. | | 14.37931 | 0. | 0. | AR2[i] |
| 30 Doublet A Lens 2 Front | −0.00328 | 10.16871 | Ge | 14.37931 | 0. | 0. | AR2[i] |
| 31 Doublet A Lens 2 Back | −0.00503 | 278.04422 | | 14.83732 | 0. | 0. | AR2[i] |
| 32 Doublet B Lens 3 Front | 0.02332 | 24.81841 | ZnSe | 10.12874 | 0. | 0. | AR2[i] |
| 33 Doublet B Lens 3 Back | 0.06189 | 0. | | 6.47069 | 0. | 0. | AR2[i] |
| 34 Doublet B Lens 4 Front | 0.06189 | 25.39288 | Ge | 6.47069 | 0. | 0. | AR2[i] |

TABLE 1-continued Example design parameters.

| SURFACE | CURVE (mm$^{-1}$) | THICK (mm) | GLASS | SEMI-DIAMETER (mm) | CONIC | X-AXIS TILT (deg) | Coating |
|---|---|---|---|---|---|---|---|
| 35 Doublet B Lens 4 Back | 0.00000 | 0.00417 | | 0.47000 | 0. | 0. | AR2[(i)] |
| 36 Image Space FPA[(g)] | 0. | 0. | | 0.46537 | 0. | 0. | |

[(a)]Circular 5.25 mm max radius,
[(b)]Circular 4.28 mm max radius,
[(c)]17.018 × 20 mm$^2$ rectangular half-widths,
[(d)]Interferometer Birefringent In,
[(e)]Interferometer Birefringent Out,
[(f)]17.018 × 36 mm$^2$ rectangular half-widths,
[(g)]50 × 50 pixels$^2$ focal-plane array,
[(h)]Brewester angle,
[(i)]2-layers antireflection coating,
[(j)]high reflectance thin aluminum layer

TABLE 2

Vignetting parameters of the sensor optical design

| Y-Field[a] (deg) | VDX[b] (mm) | VDY[c] (mm) | VCX[d] (mm) | VCY[e] (mm) |
|---|---|---|---|---|
| 37 | 0.00000 | 0.48334 | 0.12228 | 0.51652 |
| 44 | 0.00000 | 0.25005 | 0.03950 | 0.25008 |
| 51 | 0.00000 | 0.09578 | 0.01497 | 0.09579 |
| 58 | 0.00000 | 0.04934 | 0.00008 | 0.04935 |
| 65 | 0.00000 | 0.00000 | 0.00000 | 0.00000 |
| 70 | 0.00000 | 0.49996 | 0.10305 | 0.50001 |

[a]Chief ray polar angle θ in the X(horizontal)–Y(vertical) plane,
[b]null decentration of entrance pupil along the X-axis,
[c]decentration of entrance pupil along the +Y-axis,
[d]compression of entrance pupil along the +X-axis, and
[e]compression of entrance pupil along the +Y-axis.

TABLE 3

Mueller matrix $\mathfrak{M}$ for [½, ¼] waveplate state of optic $\mathcal{M}_{19-20}$ of FIG. 2b. Fundamental and overtone PEM frequencies of modulators $M_{21-22}$ and $M_{17-18}$ are $\omega_1$ and $\omega_2$, respectively. These Mueller elements are produced via a $CO_2$ carrier laser beam transmitting data and generation of a polarogram from that beam. The $\mathfrak{M}^{4,4}$ element is used for binary encryption. Optical orientations of the photopolarimeter optics of order $[P_{24-25}, M_{21-22}|M_{17-18}, P_{13-14}]$ are [vertical, −45° | +45°, verticial]

| $\mathfrak{M}^{1,1}$ | $\mathfrak{M}^{1,2}$ | $\mathfrak{M}^{1,3}$ | $\mathfrak{M}^{1,4}$ |
|---|---|---|---|
| [1, 1] (dc)[a] | [0, 0] (2ω$_1$) | NA[b] | [0, 0] (ω$_1$) |
| $\mathfrak{M}^{2,1}$ | $\mathfrak{M}^{2,2}$ | $\mathfrak{M}^{2,3}$ | $\mathfrak{M}^{2,4}$ |
| [0, 0] (2ω$_2$) | [1, 1] (2ω$_2$ − 2ω$_1$) | NA[b] | [0, 0] (ω$_1$ + 2ω$_2$) |
| $\mathfrak{M}^{3,1}$ | $\mathfrak{M}^{3,2}$ | $\mathfrak{M}^{3,3}$ | $\mathfrak{M}^{3,4}$ |
| NA[b] | NA[b] | NA[b] | NA[b] |
| $\mathfrak{M}^{4,1}$ | $\mathfrak{M}^{4,2}$ | $\mathfrak{M}^{4,3}$ | $\mathfrak{M}^{4,4}$ |
| [0, 0] (ω$_2$) | [0, 0] (2ω$_1$ + ω$_2$) | NA[b] | [−1, 0] (ω$_1$ + ω$_2$) |

[a]Scalar element of the Mueller matrix with no polarization dependence.
[b]Not accessible for measurement given Case A.

TABLE 4

Mueller matrix $\mathfrak{M}$ for [½, ¼] waveplate states of optic $\mathcal{M}_{19-20}$ of FIG. 2b. Fundamental and overtone PEM frequencies of modulators $M_{21-22}$ and $M_{17-18}$ are $\omega_1$ and $\omega_2$, respectively. These Mueller elements are produced via a $CO_2$ carrier laser transmitting data as shown in FIG. 1a and generation of a polarogram from that beam. The $\mathfrak{M}^{3,4}$ and $\mathfrak{M}^{4,4}$ elements are used for binary encryption. Optical orientations of the photopolarimeter optics of order $[P_{24-25}, M_{21-22}|M_{17-18}, P_{13-14}]$ are [vertical, −45° | vertical, −45°]

| $\mathfrak{M}^{1,1}$ | $\mathfrak{M}^{1,2}$ | $\mathfrak{M}^{1,3}$ | $\mathfrak{M}^{1,4}$ |
|---|---|---|---|
| [1, 1] (dc)[a] | [0, 0] (2ω$_1$) | NA[b] | [0, 0] (ω$_1$) |
| $\mathfrak{M}^{2,1}$ | $\mathfrak{M}^{2,2}$ | $\mathfrak{M}^{2,3}$ | $\mathfrak{M}^{2,4}$ |
| NA[b] | NA[b] | NA[b] | NA[b] |
| $\mathfrak{M}^{3,1}$ | $\mathfrak{M}^{3,2}$ | $\mathfrak{M}^{3,3}$ | $\mathfrak{M}^{3,4}$ |
| [0, 0] (2ω$_2$) | [0, 0] (2ω$_2$ − 2ω$_1$) | NA[b] | [0, −1] (ω$_1$ + 2ω$_2$) |
| $\mathfrak{M}^{4,1}$ | $\mathfrak{M}^{4,2}$ | $\mathfrak{M}^{4,3}$ | $\mathfrak{M}^{4,4}$ |
| [0, 0] (ω$_2$) | [0, 0] (2ω$_1$ + ω$_2$) | NA[b] | [−1, 0] (ω$_1$ + ω$_2$) |

[a]Scalar element of the Mueller matrix with no poliarization dependence.
[b]Not accessible for measurement given Case B.

TABLE 5

Mueller matrix $\mathfrak{M}$ for [½, ¼] waveplate states of optic $\mathcal{M}_{19-20}$ of FIG. 2b. Fundamental and overtone PEM frequencies of modulators $M_{21-22}$ and $M_{17-18}$ are $\omega_1$ and $\omega_2$, respectively. These Mueller elements are produced via a $CO_2$ carrier laser beam transmitting as shown in FIG. 1 and generation of a polarogram from that beam. The $\mathfrak{M}^{3,3}$, $\mathfrak{M}^{3,4}$, $\mathfrak{M}^{4,3}$ and $\mathfrak{M}^{4,4}$ elements are used for binary encryption. Optical orientations of the photopolarimeter optics of order $[P_{24-25}, M_{21-22}|M_{17-18}, P_{13-14}]$ are [+45°, vertical | vertical, −45°]

| $\mathfrak{M}^{1,1}$ | $\mathfrak{M}^{1,2}$ | $\mathfrak{M}^{1,3}$ | $\mathfrak{M}^{1,4}$ |
|---|---|---|---|
| [1, 1] (dc)[a] | NA[b] | [0, 0] (2ω$_1$) | [0, 0] (ω$_1$) |
| $\mathfrak{M}^{2,1}$ | $\mathfrak{M}^{2,2}$ | $\mathfrak{M}^{2,3}$ | $\mathfrak{M}^{2,4}$ |
| NA[b] | NA[b] | NA[b] | NA[b] |
| $\mathfrak{M}^{3,1}$ | $\mathfrak{M}^{3,2}$ | $\mathfrak{M}^{3,3}$ | $\mathfrak{M}^{3,4}$ |
| [0, 0] (2ω$_2$) | NA[b] | [−1, 0] (2ω$_2$ − 2ω$_1$) | [0, −1] (ω$_1$ + 2ω$_2$) |

TABLE 5-continued

Mueller matrix $\mathfrak{M}$ for [½, ¼] waveplate states of optic $\mathcal{M}_{19-20}$ of FIG. 2b. Fundamental and overtone PEM frequencies of modulators $M_{21-22}$ and $M_{17-18}$ are $\omega_1$ and $\omega_2$, respectively. These Mueller elements are produced via a $CO_2$ carrier laser beam transmitting as shown in FIG. 1 and generation of a polarogram from that beam. The $\mathfrak{M}^{33}$, $\mathfrak{M}^{34}$, $\mathfrak{M}^{43}$ and $\mathfrak{M}^{44}$ elements are used for binary encryption. Optical orientations of the photopolarimeter optics of order [$P_{24-25}$, $M_{21-22}|M_{17-18}$, $P_{13-14}$] are [+45°, vertical | vertical, −45°]

| $\mathfrak{M}^{4,1}$ | $\mathfrak{M}^{4,2}$ | $\mathfrak{M}^{4,3}$ | $\mathfrak{M}^{4,4}$ |
|---|---|---|---|
| [0, 0] ($\omega_2$) | NA[b] | [0, 1] ($2\omega_1 + \omega_2$) | [−1, 0] ($\omega_1 + \omega_2$) |

[a]Scalar element of the Mueller matrix with no polarization dependence.
[b]Not accessible for measurement given Case C.

TABLE 6

Mueller matrix $\mathfrak{M}$ for [½, ¼] waveplate states of optic $\mathcal{M}_{19-20}$ of FIG. 2b. Fundamental and overtone PEM frequencies of modulators $M_{21-22}$ and $M_{17-18}$ are $\omega_1$ and $\omega_2$, respectively. These Mueller elements are produced via a $CO_2$ carrier laser beam transmitting as shown in FIG. 1 and generation of a polarogram from that beam. The $\mathfrak{M}^{43}$ and $\mathfrak{M}^{44}$ elements are used for binary encryption. Optical orientations of the photopolarimeter optics of order [$P_{24-25}$, $M_{21-22}|M_{17-18}$, $P_{13-14}$] are [+45°, vertical | +45°, vertical]

| $\mathfrak{M}^{1,1}$ | $\mathfrak{M}^{1,2}$ | $\mathfrak{M}^{1,3}$ | $\mathfrak{M}^{1,4}$ |
|---|---|---|---|
| [1, 1] (dc)[a] | NA[b] | [0, 0] ($2\omega_1$) | [0, 0] ($\omega_1$) |
| $\mathfrak{M}^{2,1}$ | $\mathfrak{M}^{2,2}$ | $\mathfrak{M}^{2,3}$ | $\mathfrak{M}^{2,4}$ |
| [0, 0] ($2\omega_2$) | NA[b] | [0, 0] ($2\omega_2 - 2\omega_1$) | [0, 0] ($\omega_1 + 2\omega_2$) |
| $\mathfrak{M}^{3,1}$ | $\mathfrak{M}^{3,2}$ | $\mathfrak{M}^{3,3}$ | $\mathfrak{M}^{3,4}$ |
| NA[b] | NA[b] | NA[b] | NA[b] |
| $\mathfrak{M}^{4,1}$ | $\mathfrak{M}^{4,2}$ | $\mathfrak{M}^{4,3}$ | $\mathfrak{M}^{4,4}$ |
| [0, 0] ($\omega_2$) | NA[b] | [0, 1] ($2\omega_1 + \omega_2$) | [−1, 0] ($\omega_1 + \omega_2$) |

[a]Scalar element of the Mueller matrix with no polarization dependence.
[b]Not accessible for measurement given Case D.

What is claimed is:

1. A system to detect a chemical analyte in a surrounding panorama in a passive interferometer mode and to broadcast information concerning the analyte in an active photopolarimeter mode, comprising:
an optical collector that collects middle infrared radiation from a surrounding panorama;
a collimator that collimates the middle infrared radiation from the optical collector;
an interferometer comprised of a plurality of birefringent photoelastic modulators that modulate the collimated middle infrared radiance at a plurality of modulation frequencies to provide a plurality of interferograms of said collected radiance, wherein said plurality of photoelastic modulators comprises at least two end photoelastic modulators and a middle photoelastic modulator;
an imager that focuses the collected, collimated, and modulated radiance into an image;
a focal plane array that converts the image into a plurality of interferograms, or time-varying signals, mapped to coordinates in the surrounding panorama;
a spectrum analyzer that converts the plurality of interferograms, or time varying signals, into a plurality of spectra;
a processor that analyzes the plurality of spectra and provides detection data corresponding to a chemical analyte, and
a solid-state photopolarimeter comprising a carrier laser beam directed back through the plurality of birefringent photoelastic modulators, collimator, and collector, and dispersed throughout the panorama, and wherein broadcasting information is cast into the panorama via an active photopolarimeter mode wherein said middle birefringent photoelastic modulator is driven to encode the carrier laser beam to alternate half-waveplate and quarter-waveplate states such that information comprising the detection data is encrypted and broadcast omnidirectionally.

2. The system of claim 1, wherein modulation frequencies of said end birefringent photoelastic modulators operating in an interferometer mode are also used in the photopolarimeter mode of operation.

3. The system of claim 1, wherein the modulation of the carrier beam comprises binary Mueller matrix encoding.

4. The system of claim 3, wherein by states of the fourth-quadrant of the Mueller matrix are used.

5. The system of claim 1, wherein the imager is comprised of a first doublet separated by a relatively large air gap from a second doublet.

6. The system of claim 1, further comprising antireflection coatings on one or more optical surfaces of the imager.

7. The system of claim 1, wherein at least one optical component is optimized for vignetting factors and minimum limits of coma, field curvature, and distortion of image.

8. The system of claim 1, wherein the imager is optimized for an image resolution of 45 line-pairs per millimeter resolution within Modulation Transfer Function (MTF) values of 0.3-0.5 for all field angles.

9. The system of claim 1, wherein compensation is provided for changes in ambient atmospheric conditions.

10. The system of claim 9, wherein the compensation comprises isolating an interior optical volume of the system from the atmosphere.

11. The system of claim 10, wherein the interior optical volume of the system is placed under a vacuum.

12. The system of claim 1, further comprising an index-matched hydrophobic coating on an external optical surface.

13. The system of claim 1, wherein stray light and ghost imaging are minimized by a nonsequential ray tracing model.

14. The system of claim 1, further comprising a shutter that gates the carrier beam to predetermined pulse durations.

15. The system of claim 14, wherein the pulse duration is set to the periods of ½- and ¼-wave retardations of the middle birefringent photoelastic modulator driven to encode the carrier beam.

16. The system of claim 1, wherein the carrier beam comprises a polarogram data record comprising 8 of 16 Mueller matrix elements.

17. The system of claim 16, wherein a simultaneous conformation of binary data is provided over a complimentary Mueller Matrix channel.

18. The system of claim 17, wherein the simultaneous conformation of binary data is used to check for data errors.

19. A method of passively detecting and reporting the presence of a chemical analyte in a panorama through shared optical elements, comprising:
collecting middle infrared radiation from the panorama with an optical collector;
collimating the middle infrared radiation from the optical collector;

modulating the middle infrared radiation from the collector with an interferometer comprised of a plurality of solid state birefringent photoelastic modulators to provide a plurality of interferograms simultaneously generated onto a focal plane array detector grid, wherein said plurality of photoelastic modulators comprises at least two end photoelastic modulators and a middle photoelastic modulator;

focusing the collected, collimated, and modulated radiance into an image at said focal plane array detector;

converting the image into a plurality of interferograms, or time-varying signals, mapped to coordinates in the panorama at the focal plane array;

converting the plurality of interferograms, or time varying signals, into a plurality of spectra;

analyzing the plurality of spectra to provide detection data concerning the presence of targeted analytes; and directing a carrier laser beam back through the plurality of solid state birefringent photoelastic modulators, driven to encode the detection data via a binary Mueller matrix encoding, wherein a middle birefringent photoelastic modulator is driven to encode the carrier beam to alternate half-waveplate and quarter-waveplate states; and dispersing the carrier beam back into the panorama through the optical collimator and collector.

20. The method of claim 19, wherein binary Mueller matrix encoding comprises employing binary states of the fourth-quadrant elements.

21. The method of claim 19, wherein modulation frequencies of the end birefringent photoelastic modulators operating in an interferometer mode are also used in a polarimeter mode of operation.

22. The method of claim 19, wherein the modulation of the carrier beam comprises binary Mueller matrix encoding.

23. The method of claim 22, wherein binary states of the fourth-quadrant of the Mueller Matrix are used.

24. The method of claim 19, wherein the imager is comprised of a first doublet separated by a relatively large air gap from a second doublet.

25. The method of claim 19, further comprising providing antireflection coatings on one or more optical surfaces of the imager.

26. The method of claim 19, wherein at least one optical component is optimized for vignetting factors and minimum limits of coma, field curvature, and distortion of image.

27. The method of claim 19, wherein the imager is optimized for an image resolution of 45 line-pairs per millimeter resolution within Modulation Transfer Function (MTF) values of 0.3–0.5 for all field angles.

28. The method of claim 19, further comprising providing compensation for changes in ambient atmospheric conditions.

29. The method of claim 28, wherein providing compensation for changes in ambient atmospheric conditions comprises isolating an interior optical volume of the system from the atmosphere.

30. The method of claim 29, wherein the interior optical volume of the system is placed under a vacuum.

31. The method of claim 19, further comprising providing an index-matched hydrophobic coating on an external optical surface.

32. The method of claim 19, further comprising minimizing stray light and ghost imaging by employing a nonsequential ray tracing model.

33. The method of claim 19, further comprising providing a shutter that gates the carrier beam to predetermined pulse durations.

34. The method of claim 33, wherein the pulse duration is set to the periods of ½- and ¼-wave retardations of said middle birefringent photoelastic modulator driven to encode the carrier beam.

35. The method of claim 19, wherein the carrier beam comprises a polarogram data record comprising 8 of 16 Mueller matrix elements.

36. The method of claim 35, wherein a simultaneous conformation of binary data is provided over a complimentary Mueller Matrix channel.

37. The method of claim 36, wherein the simultaneous conformation of binary data is used to check for data errors.

* * * * *